United States Patent
Jia et al.

(10) Patent No.: US 10,590,169 B2
(45) Date of Patent: Mar. 17, 2020

(54) COMPOSITIONS AND METHODS FOR INHIBITING CD279 INTERACTIONS

(71) Applicant: Virogin Biotech Canada Ltd., Vancouver (CA)

(72) Inventors: William Jia, Burnaby (CA); Xuexian Bu, Surrey (CA); I-Fang Lee, Burnaby (CA)

(73) Assignee: Virogin Biotech Canada Ltd, Vancouver (CA)

( * ) Notice: Subject to any disclaimer, the term of this patent is extended or adjusted under 35 U.S.C. 154(b) by 0 days.

(21) Appl. No.: 15/374,893

(22) Filed: Dec. 9, 2016

(65) Prior Publication Data

US 2018/0141975 A1    May 24, 2018

Related U.S. Application Data

(60) Provisional application No. 62/265,296, filed on Dec. 9, 2015.

(51) Int. Cl.

| C07K 7/06 | (2006.01) |
|---|---|
| C07K 7/08 | (2006.01) |
| A61K 38/08 | (2019.01) |
| A61K 38/10 | (2006.01) |
| A61P 35/00 | (2006.01) |
| C07K 14/705 | (2006.01) |
| A61K 38/00 | (2006.01) |

(52) U.S. Cl.
CPC .......... *C07K 7/08* (2013.01); *C07K 14/70503* (2013.01); *A61K 38/00* (2013.01); *C07K 7/06* (2013.01); *C07K 2319/30* (2013.01)

(58) Field of Classification Search
None
See application file for complete search history.

(56) References Cited

U.S. PATENT DOCUMENTS

2011/0318373 A1*  12/2011  Sasikumar ........... C07K 14/705
                                                            424/185.1

FOREIGN PATENT DOCUMENTS

WO        2011161699 A2        12/2011

OTHER PUBLICATIONS

National Institute of Cancer—understanding and related topics, accessed Aug. 21, 2014 at URL: cancer.gov/cancertopics/understandingcancer, 63 pages (Year: 2017).*
Merck Manuals Lung Carcinoma accessed Mar. 12, 2017 at URL merckmanuals.com/professional/pulmonary-disorders/tumors-of-the-lungs/lung-carcinoma, 18 pages (Year: 2016).*
Merck Manuals Neuroblastoma accessed Mar. 12, 2017 at URL merckmanuals.com/professional/ pediatrics/pediatric-cancers/neuroblastoma, 4 pages (Year: 2015).*
Cholangiocarcinoma accessed Mar. 12, 2017 at URL surgery.usc.edu/divisions/tumor/pancreasdiseases/web%20pages/BILIARY%20SYSTEM/cholangiocarcinoma, 2 pages, (Year: 2002).*
Thyroid cancer accessed Mar. 12, 2017 at URL www.merckmanuals.com/professional/endocrine-and-metabolic-disorders/thyroid-disorders/thyroid-cancers, 4 pages (Year: 2016).*
Merck Manual Colorectal Cancer accessed Aug. 21, 2014 at URL merckmanuals.com/home/digestive_disorders/tumors_of_the_digestive_system/colorectal_cancer.htnn, 5 pages (Year: 2013).*
Merck Manual Prostate Cancer accessed Aug. 21, 2014 at URL: merckmanuals.com/home/kidney_and_urinary_tract_disorders/cancers_of_the_kidney_and_genitourinary_tract/prostate_cancer.html?qt=prostate cancer&alt=sh, 8 pages (Year: 2013).*
Renal cell carcinoma, accessed Mar. 12, 2017 at URL merckmanuals.com/professional/genitourinary-disorders/genitourinary-cancer/renal-cell-carcinoma, 6 pages (Year: 2013).*
Merck Manual Bladder Cancer accessed Aug. 21, 2014 at URL: merckmanuals.com/home/kidney_and_urinary_tract_disorders/cancers_of_the_kidney_and_genitourinary_tract/bladder_cancer.html, 2 pages (Year: 2014).*
McDermott et al., "PD-1 as a potential target in cancer therapy," Cancer Medicine 2(5): 662-673 (2013) (Year: 2013).*
Teng et al., "Classifying Cancers BasedonT-cell Infiltration and PD-L1," Am. Assoc. Cancer Res. J. 75:2139-2145 (2015) (Year: 2015).*
Kiesler, "Why a New Immunotherapy for Lung Cancer Works for Only Some People," accessed Feb. 12, 2018 at URL mskcc.org/blog/why-new-immunotherapy-lung-works-only-some-people (Apr. 2015; pp. 1-4)) (Year: 2015).*
European Search Report dated Apr. 3, 2018, for Application No. 17198390.1.
Sasikumar, Pottayil G. et al., "Abstract 1231: Equipotent antagonism, transient immune activation and excellent antitumor efficacy with a peptide inhibitor of PD-1 immune check point pathway", Cancer Research, v. 73, No. 8, Apr. 15, 2013.

* cited by examiner

*Primary Examiner* — Julie Ha
*Assistant Examiner* — Kristina M Hellman
(74) *Attorney, Agent, or Firm* — Kurious LLC

(57) ABSTRACT

Methods and compositions for inhibiting and/or interfering with interactions between (1) programmed Death-1 protein (also known as CD279) and (2) programmed death-ligand 1 (PD-L1) and/or programmed death-ligand 2 (PD-L2) are disclosed. In addition, methods and compositions for increasing IL-2 levels in a cell, and methods and compositions for preventing, treating, or ameliorating the effects of cancer in a subject, are disclosed.

10 Claims, 12 Drawing Sheets
Specification includes a Sequence Listing.

Human WT peptide: WYRMSPSNQT (SEQ ID NO:1)
Mouse WT peptide: WNRLSPSNQT (SEQ ID NO:35)

Human TF peptide: TAHPSPSPRSAGQF (SEQ ID NO:2)
Mouse TF peptide: TRYPSPSPKPEGRF (SEQ ID NO:36)

(The underlined amino acids represent the differences between human and mouse)

COMPOSITIONS AND METHODS FOR INHIBITING CD279 INTERACTIONS

CROSS-REFERENCE TO RELATED APPLICATIONS

This application claims priority to, and incorporates by reference, U.S. provisional patent application Ser. No. 62/265,296, filed Dec. 9, 2015.

FIELD OF THE INVENTION

The field of the present invention relates to certain compositions and methods that are useful in preventing, treating, and/or ameliorating the effects of various types of cancers. More particularly, the field of the present invention relates to certain compositions and methods that may be used to inhibit PD-1/PD-L1 and/or PD-1/PD-L2 interactions, which may further be useful in preventing, treating, and/or ameliorating the effects of various types of cancers.

BACKGROUND OF THE INVENTION

The Programmed Death-1 (PD-1) protein, also known as CD279, is an inhibitory receptor that belongs to the CD28 family of receptors. PD-1 is expressed on activated T cells, B cells, and myeloid cells and contains a membrane proximal immune-receptor tyrosine inhibitory motif (ITIM) and a membrane distal tyrosine-based switch motif (ITSM). PD-1 has been reported as an immune checkpoint, and to serve an important role in down-regulating the immune system by preventing the activation of T cells. Ligation of PD-1 by its ligands has been found to generate an inhibitory signal that results in reduced cytokine production, and reduced T cell survival. Two ligands for PD-1 have previously been identified, which have been referred to, in the prior art, as programmed death-ligand 1 (PD-L1) (B7-H1) and programmed death-ligand 2 (PD-L2) (B7-DC), and have been shown to down-regulate T cell activation upon binding to PD-1. Moreover, the interaction between PD-1 and PD-L1 has also been found to result in a decrease in tumor infiltrating lymphocytes, a decrease in T-cell receptor mediated proliferation, and immune evasion by the cancerous cells.

In view of the foregoing, it would be desirable to identify and develop one or more peptides that are effective to compete with PD-L1 and/or PD-L2 for binding to PD-1, which may thereby inhibit PD-1/PD-L1 and/or PD-1/PD-L2 interactions. Such inhibitory effects will preferably be useful in preventing, treating, and/or ameliorating the effects of various types of cancers. As the following will demonstrate, the present invention provides such peptides, methods for using such peptides, and other advantages described herein.

SUMMARY OF THE INVENTION

According to certain aspects of the present invention, isolated and purified peptides are provided that are represented by the amino acid sequences of SEQ ID NO:1, SEQ ID NO:2, derivatives thereof (such as SEQ ID NO:3-SEQ ID NO:36), and combinations thereof. In addition, the invention encompasses isolated and purified peptides that are substantially homologous to SEQ ID NO:1, SEQ ID NO:2, derivatives thereof, and combinations thereof, such as at least 80%, 90%, or 95% homologous to SEQ ID NO:1, SEQ ID NO:2, SEQ ID NO:3-SEQ ID NO:36, and combinations thereof. Still further, the present invention encompasses fragments and elongated forms of SEQ ID NO:1, SEQ ID NO:2, and derivatives thereof, as well as nucleic acid sequences and vectors (e.g., viral vectors, such as HSV-1) that encode such peptides or derivatives thereof. Moreover, the present invention encompasses pharmaceutical-grade compositions that comprise a peptide consisting of an amino acid sequence of SEQ ID NO:1, SEQ ID NO:2, derivatives thereof, and combinations thereof (along with fragments thereof, elongated forms thereof, and peptides that are substantially homologous to SEQ ID NO:1, SEQ ID NO:2, derivatives thereof, and combinations thereof).

According to additional aspects of the present invention, methods of using the compositions described herein are provided. More particularly, for example, the invention encompasses methods for inhibiting interactions between PD-1 and PD-L1 in one or more cells by administering a composition described herein, such as an amino acid sequence of SEQ ID NO:1, SEQ ID NO:2, derivatives thereof (such as those of SEQ ID NO:3-SEQ ID NO:36), peptides that are substantially homologous to the foregoing peptides, or pharmaceutical-grade compositions that comprise any of such peptides. Likewise, the present invention encompasses methods for increasing IL-2 levels in one or more cells by administering a composition described herein, such as an amino acid sequence of SEQ ID NO:1, SEQ ID NO:2, derivatives thereof, combinations thereof, peptides that are substantially homologous to any of such peptides, or pharmaceutical-grade compositions that comprise any of such peptides. Still further, the present invention encompasses methods for preventing, treating, or ameliorating the effects of cancer in a subject by administering an effective amount of a composition described herein, such as an amino acid sequence of SEQ ID NO:1, SEQ ID NO:2, derivatives thereof, combinations thereof, peptides that are substantially homologous to any of such peptides, or pharmaceutical-grade compositions that comprise any of such peptides.

According to yet further aspects of the invention, certain derivatives of SEQ ID NO:1 are provided (such as those of SEQ ID NO:3-SEQ ID NO:36), along with peptides that are substantially homologous to the foregoing peptides. More particularly, such embodiments of the invention include peptides consisting of an amino acid sequence selected from the group consisting of SEQ ID NO:3-SEQ ID NO:36, along with sequences that are substantially homologous thereto and pharmaceutical-grade compositions that comprise such peptides. Still further, according to related embodiments, the invention encompasses (i) methods for inhibiting interaction between PD-1 and PD-L1 in one or more cells, (ii) methods for increasing IL-2 levels in one or more cells, and (iii) methods for preventing, treating, or ameliorating the effects of cancer in a subject, by administering an effective amount of one or more of such derivative peptides to the subject.

The above-mentioned and additional features of the present invention are further illustrated in the Detailed Description contained herein.

BRIEF DESCRIPTION OF THE SEQUENCE LISTING

| SEQ ID NO. | Sequence | Description |
|---|---|---|
| 1 | WYRMSPSNQT | Peptide referred to herein as "WT" |
| 2 | TAHPSPSPRSAGQF | Peptide referred to herein as "TF" |

-continued

| SEQ NO. ID. | Sequence | Description |
|---|---|---|
| 3 | WYRMSPSNQD | A derivative of the WT peptide |
| 4 | WYRMSPSNQE | A derivative of the WT peptide |
| 5 | WYRMSPSNDT | A derivative of the WT peptide |
| 6 | WYRMSPSNET | A derivative of the WT peptide |
| 7 | WYRMSPSEQT | A derivative of the WT peptide |
| 8 | WYRMSPDNQT | A derivative of the WT peptide |
| 9 | WYRMSPENQT | A derivative of the WT peptide |
| 10 | WYRMSPPNQT | A derivative of the WT peptide |
| 11 | WYRMSDSNQT | A derivative of the WT peptide |
| 12 | WYRMSESNQT | A derivative of the WT peptide |
| 13 | WYRMAPSNQT | A derivative of the WT peptide |
| 14 | WYRMQPSNQT | A derivative of the WT peptide |
| 15 | WYRMMPSNQT | A derivative of the WT peptide |
| 16 | WYRMPPSNQT | A derivative of the WT peptide |
| 17 | WYRDSPSNQT | A derivative of the WT peptide |
| 18 | WYRESPSNQT | A derivative of the WT peptide |
| 19 | WYIMSPSNQT | A derivative of the WT peptide |
| 20 | WYLMSPSNQT | A derivative of the WT peptide |
| 21 | WYYMSPSNQT | A derivative of the WT peptide |
| 22 | WYVMSPSNQT | A derivative of the WT peptide |
| 23 | DYRMSPSNQT | A derivative of the WT peptide |
| 24 | QYRMSPSNQT | A derivative of the WT peptide |
| 25 | EYRMSPSNQT | A derivative of the WT peptide |
| 26 | MYRMSPSNQT | A derivative of the WT peptide |
| 27 | TYRMSPSNQT | A derivative of the WT peptide |
| 28 | YYRMSPSNQT | A derivative of the WT peptide |
| 29 | WYRMSWSNQT | A derivative of the WT peptide |
| 30 | WYRMYPSNQT | A derivative of the WT peptide |
| 31 | WYRNSPSNQT | A derivative of the WT peptide |
| 32 | WYTMSPSNQT | A derivative of the WT peptide |
| 33 | FQGASRPSPSPHAT | Peptide referred to herein as "D-FT" |
| 34 | TQNSPSMRYW | Peptide referred to herein as "D-TW" |
| 35 | WNRLSPSNQT | Mouse WT peptide |
| 36 | TRYPSPSPKPEGRF | Mouse TF peptide |

DETAILED DESCRIPTION OF THE INVENTION

Figure 1:
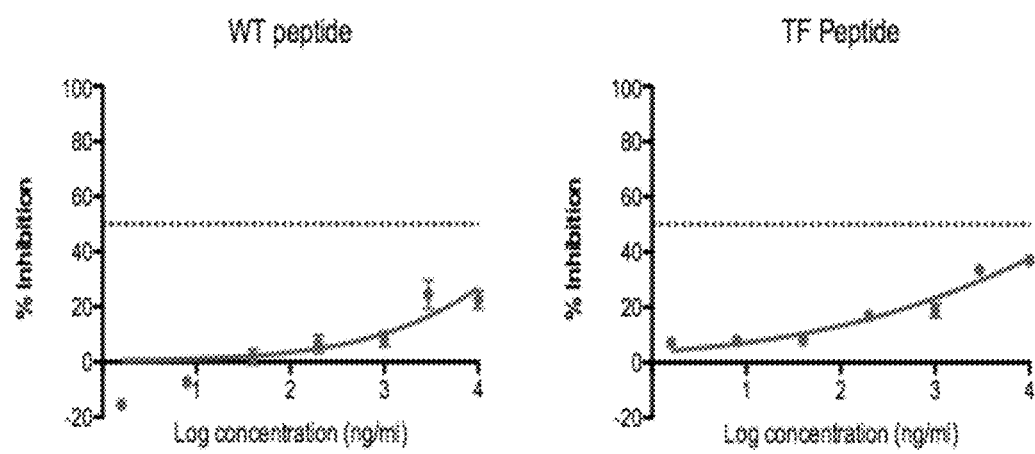
FIG. 1 is a graph showing ELISA competition results of WT (SEQ ID NO:1) and TF (SEQ ID NO:2) peptides, and the inhibitory efficacy on PD-1/PD-L1 interaction.

The following will describe in detail several preferred embodiments of the present invention. These embodiments are provided by way of explanation only, and thus, should not unduly restrict the scope of the invention. In fact, those of ordinary skill in the art will appreciate upon reading the present specification and viewing the present drawings that the invention teaches many variations and modifications, and that numerous variations of the invention may be employed, used and made without departing from the scope and spirit of the invention.

According to certain preferred embodiments of the present invention, isolated and purified peptides are provided that are represented by the amino acid sequences of SEQ ID NO:1, SEQ ID NO:2, combinations thereof, and derivatives thereof (such as those of SEQ ID NO:3-SEQ ID NO:36). In addition, the invention encompasses isolated and purified peptides that are substantially homologous to SEQ ID NO:1, SEQ ID NO:2, combinations thereof, derivatives thereof, elongated forms thereof, and fragments thereof, including peptides that are at least 80%, 90%, or 95% homologous to SEQ ID NO:1, SEQ ID NO:2, derivatives thereof (such as those of SEQ ID NO:3-SEQ ID NO:36), and combinations thereof. Still further, the present invention encompasses pharmaceutical-grade compositions that comprise a peptide consisting of an amino acid sequence of SEQ ID NO:1, SEQ ID NO:2, combinations thereof, elongated forms thereof, fragments thereof, and derivatives thereof (such as those of SEQ ID NO:3-SEQ ID NO:36), as well as peptides that are substantially homologous to the foregoing peptides.

The peptides of the present invention may be produced via chemical synthesis methods that are well-known in the art. For example, the peptides may be chemically synthesized using automated Merrifield techniques of solid phase synthesis with the α-N H$_2$ protected by either t-Boc or F-moc chemistry, using side chain protected amino acids on, for example, an Applied Biosystems Peptide Synthesizer. The peptides of the present invention may also be produced using recombinant DNA technology, including nucleic acid molecules, vectors, and/or host cells. As such, nucleic acid molecules encoding the peptides described herein are also encompassed by the present invention. Similarly, vectors, including expression vectors, comprising nucleic acid molecules, as well as host cells containing the vectors, are also encompassed by the present invention.

Still further, the invention provides that certain fragments and derivatives of the peptides represented by SEQ ID NO:1-SEQ ID NO:36 are encompassed by the present invention. For example, the peptides represented by SEQ ID NO:1-SEQ ID NO:36 may be modified by substituting one or more amino acid residues within such peptides, particularly so-called conservative amino acid substitutions, e.g., an amino acid may be substituted with an alternative amino acid having similar properties (i.e., substitutions within the same class of amino acid residues summarized below). For purposes of illustration, substitutions may be grouped into six classes based on common side chain (or "R-group") properties and the highest frequency of substitution in homologous proteins in nature, as determined, for example, by a standard Dayhoff frequency exchange matrix. The table below represents an example of such classes:

| Class | Residues | Description |
| --- | --- | --- |
| Class I | Cysteine | |
| Class II | Serine, Threonine, Proline, Hydroxyproline, Alanine, and Glycine | Small aliphatic and OH-group side chains |
| Class III | Asparagine, Aspartic acid, Glutamic acid, and Glutamine | Neutral and negatively charged side chains capable of forming hydrogen bonds |
| Class IV | Histidine, Arginine, and Lysine | Basic polar side chains |
| Class V | Isoleucine, Valine, Leucine, and Methionine | Branched aliphatic side chains (except Met) |
| Class VI | Phenylalanine, Tyrosine, and Tryptophan | Aromatic side chains |

In addition, each of the above classes may further include related amino acid analogs, such as ornithine, homoarginine, N-methyl lysine, dimethyl lysine, or trimethyl-lysine in class IV, and a halogenated tyrosine in class VI.

Furthermore, the peptides described herein may be modified through systematic substitution of one or more amino acids with a D-amino acid of the same type (e.g., D-lysine in place of L-lysine), which may be implemented to generate more stable peptides. Thus, a peptide derivative or peptidomimetic of the present invention may be all L, all D or mixed D, L peptide, in either forward or reverse order. The presence of an N-terminal or C-terminal D-amino acid increases the in vivo stability of a peptide, since peptidases cannot utilize a D-amino acid as a substrate. Reverse-D peptides are peptides containing D-amino acids, arranged in a reverse sequence relative to a peptide containing L-amino acids. For example, SEQ ID NO:33 represents the reverse, D-amino acid version of TF (SEQ ID NO:2); and SEQ ID NO:34 represents the reverse, D-amino acid version of WT (SEQ ID NO:1). Thus, the C-terminal residue of an L-amino acid peptide becomes N-terminal for the D-amino acid peptide, and so forth. Reverse D-peptides retain the same secondary conformation and therefore similar activity, as the L-amino acid peptides, but are more resistant to enzymatic degradation in vitro and in vivo, and thus can have greater therapeutic efficacy than the original peptide. Similarly, a reverse L peptide may be generated using standard methods where the C-terminus of the parent peptide takes the place of the N-terminus of the reverse L peptide. The invention provides that reverse L peptides of L-amino acid peptides that do not have significant secondary structure (e.g., short peptides) retain the same spacing and conformation of the side chains of the L-amino acid peptide and, therefore, often have similar activity as the original L-amino acid peptide. Moreover, a reverse peptide may contain a combination of L-and D-amino acids. The spacing between amino acids and the conformation of the side chains may be retained resulting in similar activity as the original L-amino acid peptide.

Still further, the peptides of the present invention may be modified to include labels and/or linkers appended thereto, which may be used for imaging purposes, for drug delivery purposes, or to provide additional therapeutic payload. For example, the peptides of the present invention may be fused to a human IgG C-domain, with the IgG antibody being designed to target and combat tumor cells. Still further, the peptides of the present invention may be fused or linked to a fragment crystallisable (Fc) region of an antibody. In addition, the peptides of the present invention include fragments, and elongated forms, of the peptides represented by SEQ ID NO:1-SEQ ID NO:36. According to yet further embodiments, the peptides of the present invention may be chemically and/or structurally modified, e.g., to increase the amount of time that the peptides will remain active in a biological system (or to otherwise improve the pharmacokinetics of the peptides). For example, the peptides may be modified to include various chemical groups, molecules, or structural adjustments, such as glycosylation, acetylation, acylation, ADP-ribosylation, amidation, covalent attachment to polyethylene glycol (e.g., PEGylation), covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, demethylation, formation of covalent cross-links, formylation, gamma carboxylation, GPI anchor formation, hydroxylation, iodination, methylation, myristoylation, oxidation, proteolytic processing, phosphorylation, prenylation, racemization, selenoylation, sulfation, ubiquitination, modifications with fatty acids, and various other modifications that may be designed to improve the pharmacokinetics of the peptides.

The invention provides that the term "peptide," as used herein, may include not only molecules in which amino acid residues are joined by the conventional peptide (—CO—NH—) linkages, but also molecules in which the peptide bond is reversed. Such retro-inverso peptidomimetics may be produced using methods known in the art, such as those described in Meziere et al (1997) J. Immunol. 159, 3230-3237 (such approach involves producing pseudopeptides containing changes involving the backbone, and not the orientation of amino acid side chains).

The invention provides that the individual peptides encompassed by the invention may be administered to a targeted cell (or a plurality of cells) directly or, alternatively, may be administered indirectly by expression from an encoding sequence. For example, a polynucleotide (nucleic acid sequence) may be provided to a cell or subject that encodes a peptide of the invention, such as any of the peptides represented by SEQ ID NO:1-SEQ ID NO:36, as well as modified forms thereof. A peptide of the invention may thus be produced from or delivered in the form of a polynucleotide which encodes, and is capable of expressing, a peptide of the present invention. Any reference herein to the use, delivery or administration of a peptide of the invention is intended to include the indirect use, delivery or administration of such a peptide via expression from a polynucleotide that encodes the peptide.

More particularly, a nucleic acid molecule of the invention may be provided in isolated or purified form, which encodes a selected peptide of the present invention, which may be transcribed (in the case of DNA) and translated (in the case of mRNA) into a peptide in vivo when placed under the control of appropriate regulatory sequences. The boundaries of the peptide encoding sequence are determined by a start codon at the 5' (amino) terminus and a translation stop codon at the 3' (carboxy) terminus. For the purposes of the present invention, such nucleic acid sequences can include, but are not limited to, cDNA from viral, prokaryotic or eukaryotic mRNA, genomic sequences from viral or prokaryotic DNA or RNA, and even synthetic DNA sequences. The nucleic acid molecules of the present invention may be synthesized according to methods well-known in the art, as described by way of example in Sambrook et al (19104, Molecular Cloning—a laboratory manual; Cold Spring Harbor Press). The nucleic acid molecules of the present invention may then be provided in the form of an expression cassette, which includes control sequences operably linked to the peptide-encoding sequence, thus allowing for expression of the applicable peptide of the invention in vivo in a targeted cell or subject. These expression cassettes, in turn, are typically provided within vectors, e.g., plasmids or recombinant viral vectors, such as herpes simplex virus 1 (HSV-1). For example, an expression cassette may be administered directly to a host cell or subject—or, alternatively, a vector comprising a peptide-encoding nucleic acid of the invention may be administered to a host cell or subject. Methods for delivering exogenous nucleic acid sequences to a host cell or subject are well-known in the art, as described in, for example, U.S. Pat. Nos. 5,399,346, 5,580,859 and 5,510,466, which are hereby incorporated by reference.

Still further, the invention provides that isolated and purified forms of the peptides described herein, including various combinations and mixtures of such peptides, may be directly administered to a host cell or subject. For example, such peptides may be administered along with pharmaceutically acceptable (pharmaceutical-grade) carriers, diluents and adjuvants, such as Dulbecco's phosphate buffered saline, pH about 7.4; 0.9% saline (0.9% w/v NaCl); and 5% (w/v) dextrose. The pharmaceutically acceptable (pharmaceutical-grade) carriers, diluents and adjuvants used to deliver a peptide of the present invention to a target cell will, preferably, not induce an immune response in the individual (subject) receiving the peptide (and will preferably be administered without undue toxicity). Additional pharmaceutically acceptable excipients include, but are not limited to, water, saline, polyethyleneglycol, hyaluronic acid and ethanol. Pharmaceutically acceptable salts can also be included therein, e.g., mineral acid salts (such as hydrochlorides, hydrobromides, phosphates, sulfates, and the like) and the salts of organic acids (such as acetates, propionates, malonates, benzoates, and the like). A thorough discussion of pharmaceutically acceptable carriers, diluents and adjuvants is available in Remington's Pharmaceutical Sciences (Mack Pub. Co., N.J. 1991).

As described above, the present invention encompasses certain methods of using the peptides described herein. More particularly, for example, the invention encompasses methods for inhibiting interactions between PD-1 and PD-L1 in one or more cells by administering one or more peptides described herein to one or more targeted cells, such as an amino acid sequence of SEQ ID NO:1 or SEQ ID NO:2, combinations thereof, fragments thereof, elongated forms thereof, derivatives thereof (such as those of SEQ ID NO:3-SEQ ID NO:36), peptides that are substantially homologous to the foregoing peptides, or pharmaceutical-grade compositions (such as those described above) that comprise any of such peptides. Likewise, the present invention encompasses methods for increasing IL-2 levels in one or more cells by administering one or more peptides described herein, such as an amino acid sequence of SEQ ID NO:1 or SEQ ID NO:2, combinations thereof, fragments thereof, elongated forms thereof, derivatives thereof (such as those of SEQ ID NO:3-SEQ ID NO:36), peptides that are substantially homologous to the foregoing peptides, or pharmaceutical-grade compositions that comprise any of such peptides. Still further, the present invention encompasses methods for preventing, treating, or ameliorating the effects of cancer in a subject by administering an effective amount of one or more peptides described herein, such as an amino acid sequence of SEQ ID NO:1 or SEQ ID NO:2, combinations thereof, fragments thereof, elongated forms thereof, derivatives thereof (such as those of SEQ ID NO:3-SEQ ID NO:36), peptides that are substantially homologous to the foregoing peptides, or pharmaceutical-grade compositions that comprise any of such peptides.

As described above, according to yet further embodiments of the invention, certain derivatives of SEQ ID NO:1 may be used in the methods referenced above. More particularly, peptides consisting of (or, in other embodiments, comprising) an amino acid sequence selected from the group consisting of SEQ ID NO:3-SEQ ID NO:36, or combinations thereof, fragments thereof, elongated forms thereof, peptides that comprise amino acid sequences that are substantially homologous thereto, and pharmaceutical-grade compositions that comprise such peptides may be used in the methods referenced above. More particularly, such derivative peptides may be used to carry out (i) methods for inhibiting interaction between PD-1 and PD-L1 in one or more cells, (ii) methods for increasing IL-2 levels in one or more cells, and (iii) methods for preventing, treating, or ameliorating the effects of cancer in a subject, by administering an effective amount of one or more of such derivative peptides.

The invention provides that the peptides of the present invention, or the nucleic acid sequences encoding one or more peptides of the present invention, should be administered to a cell or subject in an amount that effective to achieve the desired endpoint. For particularly, peptides of the present invention, or the nucleic acid sequences encoding one or more peptides of the present invention, should be administered to a cell or subject in an amount that is effective to (i) inhibit interaction between PD-1 and PD-L1 in the targeted cells, (ii) increase IL-2 levels in the targeted cells, and/or (iii) prevent, treat, or ameliorate the effects of cancer in the targeted subject. The invention provides that the peptides described herein may be administered to a cell or subject in combination or sequence with other agents that exhibit similar properties (e.g., when the peptides described herein are being administered to prevent, treat, or ameliorate the effects of cancer, the peptides may be administered to a cell or subject in combination or in series with other agents that are effective to prevent, treat, or ameliorate the effects of cancer).

The amount administered to a cell or subject will depend on a variety of factors. For example, in the case of a therapeutic use of the peptides, the amount may vary depending on the size/weight of the subject and the route of administration, such as orally (e.g. in the form of tablets, troches, lozenges, aqueous or oily suspensions, dispersible powders or granules), parenterally, epicutaneously, subcutaneously, by inhalation, intravenously, intramuscularly, intrasternally, transdermally, intradermally, sublingually, instranasally, buccally or by infusion techniques. By way of further illustration (and not limitation), the amount of the peptide(s) administered may be in the range of about 5 µg to about 100 mg of peptide; or between about 300 µg and about 1 mg of peptide; or amounts in the realm of 300 µg, 350 µg, 400 µg, 450 pg, 500 µg, 550 µg, 600 µg, 650 µg, 700 µg, 750 µg, 800 µg, 850 µg, 900 µg, 950 µg or 1 mg of the applicable peptide (or mixture of peptides).

EXAMPLES

Using a peptide array method, two peptides (SEQ ID NO:1 and SEQ ID NO:2) were discovered and chemically synthesized, which are referred to herein as WT and TF, respectively. SEQ ID NO:1/WT represents the sequence of WYRMSPSNQT. SEQ ID NO:2/TF represents the sequence of TAHPSPSPRPAGQF. As the following will demonstrate, WT and TF (and various derivatives thereof) bind to PD-L1 and prevent PD-L1 from interacting with PD-1. More particularly, as described further below, a series of experiments were performed to assess the inhibitory efficacy of the WT and TF peptides (and certain derivatives thereof) on PD-1/PD-L1 interaction (as well as the impact of such inhibition on IL-2 levels).

FIG. 1 shows ELISA competition results of the WT and TF peptides. The binding of the WT or TF peptide to human PD-L1 was tested via competition ELISA. Varying concentrations of each peptide (0.008 µg/ml to 10 µg/ml) were mixed with a fixed concentration of recombinant human PD-1 Fc (10 ng/ml) and bound to a human PD-L1 Fc coated 96-well Immuno Maxisorp flat bottom plate. Binding was detected via a biotinylated anti-PD-1 antibody, streptavidin-horseradish peroxidase (HRP), and 3,3',5,5'-Tetramethylbenzidine (TMB) substrate. Absorbance measurements were collected at 450 nm via a plate reader. The absorbance readings were plotted against the test peptide concentration. As shown in FIG. 1, as test peptide (WT, TF) concentrations increased, the percent (%) inhibition increased (i.e., the ability of the test peptide to interfere with PD-1/PD-L1 interaction increased).

Figure 2A:
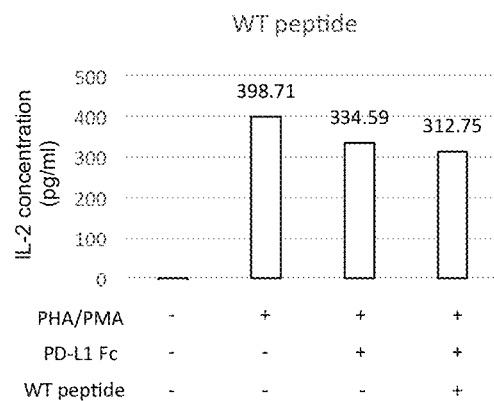
FIG. 2A is a graph showing in vitro assay results of WT peptide on inhibiting PD-1/PD-L1 interaction.
Figure 2B:
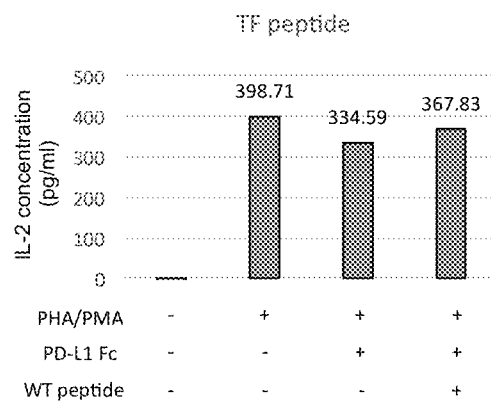
FIG. 2B is a graph showing in vitro assay results of TF peptide on inhibiting PD-1/PD-L1 interaction.
Figure 2C:
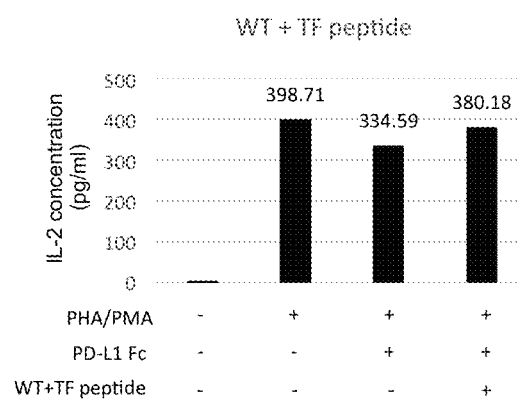
FIG. 2C is a graph showing in vitro assay results of a combination of WT and TF peptides on inhibiting PD-1/PD-L1 interaction.

FIG. 2 shows in vitro assay results of WT, TF, or combined WT and TF peptides on inhibiting PD-1/PD-L1 interaction (and the resulting effects on IL-2 concentration). 5×10⁴ Jurkat T cells were activated with 1 µg/ml of phytohemagglutinin (PHA) and 50 ng/ml of phorbol 12-myristate 13-acetate (PMA) and co-cultured with recombinant human PD-L1 Fc (8 µg/ml) plus 1-10 µg/ml of WT (FIG. 2A), 1-10 µg/ml of TF (FIG. 2B), or 1-10 µg/ml of combined WT and TF (FIG. 2C) peptide at 37° C. for 48 hours. Cell culture supernatant was harvested and interleukin-2 (IL-2) production from Jurkat T cells was assessed by IL-2 ELISA. The numbers shown above each bar in FIG. 2 represent IL-2 concentrations. As shown in FIG. 2, the presence of TF peptide, and the combined WT and TF peptides, yielded an increase in IL-2 concentration, when administered along with PD-L1 Fc.

Figure 3A:
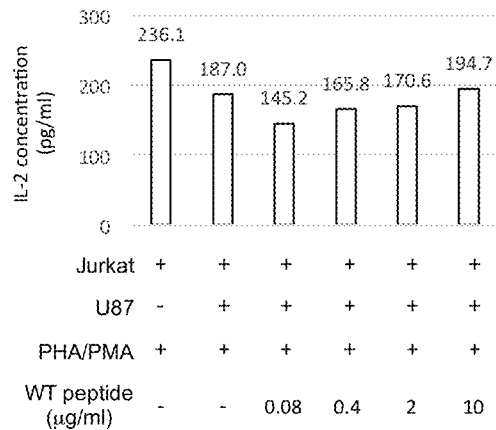
FIG. 3A is a graph showing cell-based assay results of WT peptide treatment inhibiting PD-1/PD-L1 interaction.
Figure 3B:
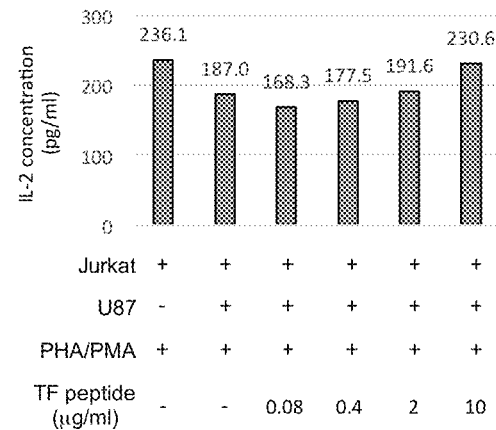
FIG. 3B is a graph showing cell-based assay results of TF peptide treatment inhibiting PD-1/PD-L1 interaction.
Figure 3C:
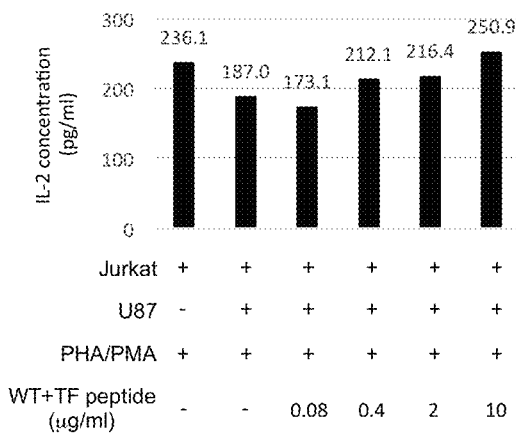
FIG. 3C is a graph showing cell-based assay results of WT and TF peptide treatment inhibiting PD-1/PD-L1 interaction.

FIG. 3 shows cell-based assay results of WT, TF, or combined WT and TF peptide treatments inhibiting PD-1/PD-L1 interaction. In this Example, 5×10⁴ Jurkat T cells were activated with 1 µ/ml of PHA and 50 ng/ml of PMA and co-cultured with 3×10⁵ PD-L1-expressed U87 tumor cells mixed with different concentrations of WT (FIG. 3A), TF (FIG. 3B), or combined WT and TF (FIG. 3C) peptide at 37° C. for 48 hours. Cell culture supernatants were harvested and IL-2 production from the Jurkat T cells was assessed by IL-2 ELISA. The numbers shown above each bar in FIGS. 3A-3C represent IL-2 concentrations. As shown in FIGS. 3A-3C, the presence of WT peptide, TF peptide, and the combined WT and TF peptides yielded an increase in IL-2 concentration, when administered along with PD-L1 Fc. Moreover, as shown in FIGS. 3A-3C, as the concentrations of the test peptides were increased, an increase in IL-2 concentration was observed.

Figure 4:
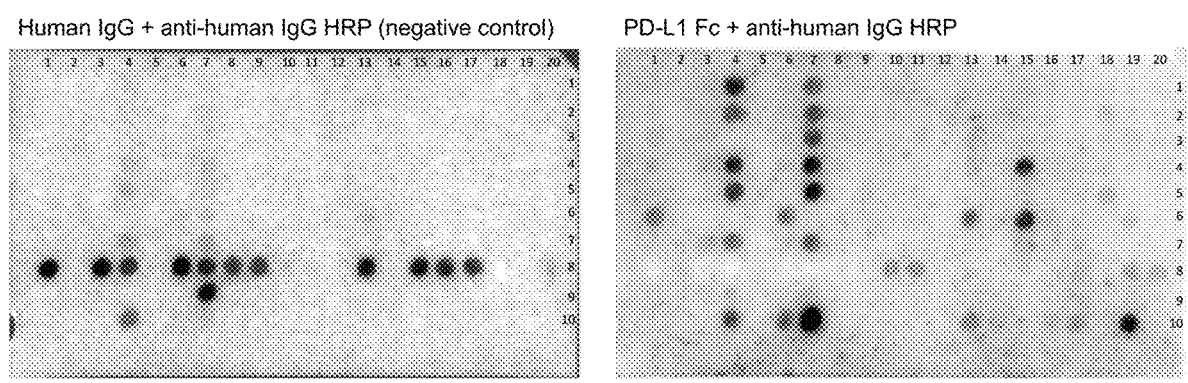
FIG. 4 shows the peptide array results described herein.

The foregoing assay results demonstrate that both WT and TF peptides are able to block PD-1/PD-L1 interaction. In addition, when the WT and TF peptides are combined, an enhanced inhibitory effect is observed (relative to a single test peptide treatment). To improve the binding affinity of the WT peptide, a single amino acid was substituted at each position of the WT peptide and the binding affinities of such derivative peptides for PD-L1 was examined via peptide arrays. More particularly, peptide array results were generated by incubating derivative test peptide-containing membrane with 15 µg/ml of negative control human IgG or recombinant human PD-L1 Fc at 4° C., overnight. The resulting signals were detected by HRP-conjugated anti-human IgG and HRP substrate. Referring now to FIG. 4, each dot shown therein represents a detected signal from interactions between a test derivative peptide and human PD-L1 Fc, with the depth of black color being indicative of the level of binding affinity. Based on the peptide array results in FIG. 4, the following sequences of derivative peptides were developed as alternatives to the WT peptide:

| SEQ ID. NO. | Sequence |
| --- | --- |
| 3 | WYRMSPSNQD |
| 4 | WYRMSPSNQE |
| 5 | WYRMSPSNDT |

| SEQ ID. NO. | Sequence |
| --- | --- |
| 6 | WYRMSPSNET |
| 7 | WYRMSPSEQT |
| 8 | WYRMSPDNQT |
| 9 | WYRMSPENQT |
| 10 | WYRMSPPNQT |
| 11 | WYRMSDSNQT |
| 12 | WYRMSESNQT |
| 13 | WYRMAPSNQT |
| 14 | WYRMQPSNQT |
| 15 | WYRMMPSNQT |
| 16 | WYRMPPSNQT |
| 17 | WYRDSPSNQT |
| 18 | WYRESPSNQT |
| 19 | WYIMSPSNQT |
| 20 | WYLMSPSNQT |
| 21 | WYYMSPSNQT |
| 22 | WYVMSPSNQT |
| 23 | DYRMSPSNQT |
| 24 | QYRMSPSNQT |
| 25 | EYRMSPSNQT |
| 26 | MYRMSPSNQT |
| 27 | TYRMSPSNQT |
| 28 | YYRMSPSNQT |
| 29 | WYRMSWSNQT |
| 30 | WYRMYPSNQT |
| 31 | WYRNSPSNQT |
| 32 | WYTMSPSNQT |
| 34 | TQNSPSMRYW |
| 35 | WNRLSPSNQT |

Figure 5A:
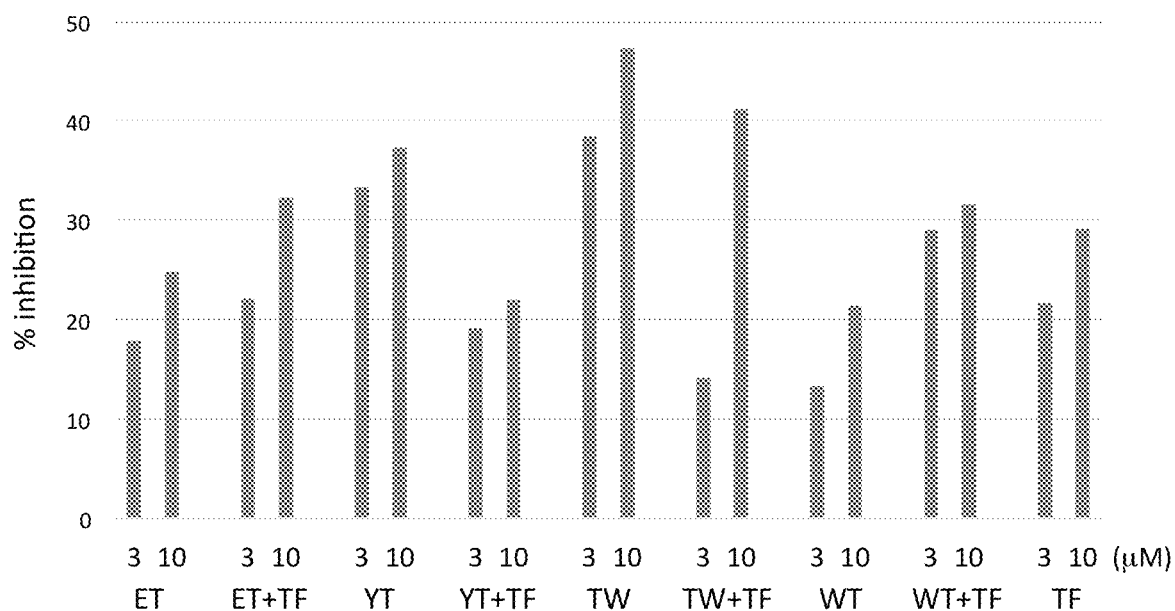
FIG. 5A summarizes the results of an ELISA assay, which shows blocking PD-L1 binding to PD-1 by combined PD-L1 blocking peptides.

FIG. 5A shows blocking PD-L1 binding to PD-1 by certain PD-L1 blocking peptides (and certain combinations thereof). More particularly, in this Example and referring to FIGS. 5A and 5B, WT represents SEQ ID NO:1; TF represents SEQ ID NO:2; ET represents SEQ ID NO:25; YT represents SEQ ID NO:28; and TW represents the reverse sequence of WT with D-amino acids, SEQ ID NO:34 (also referred to herein as "D-TW"). Different combination of such PD-L1 blocking peptides (3 and 10 µM) were mixed with recombinant human PD-1 Fc and bound to a human PD-L1 Fc coated 96-well Immuno Maxisorp flat bottom plate. Binding was detected via a biotinylated anti-PD-1 antibody, streptavidin-horseradish peroxidase (HRP), and 3,3', 5,5'-Tetramethylbenzidine (TMB) substrate. Absorbance measurements were collected at 450 nm via a plate reader. The increased percent (%) of human PD-1/PD-L1 inhibition was compared to a sample that was not provided with a test peptide. The results are summarized in FIG. 5A.

Figure 5B:
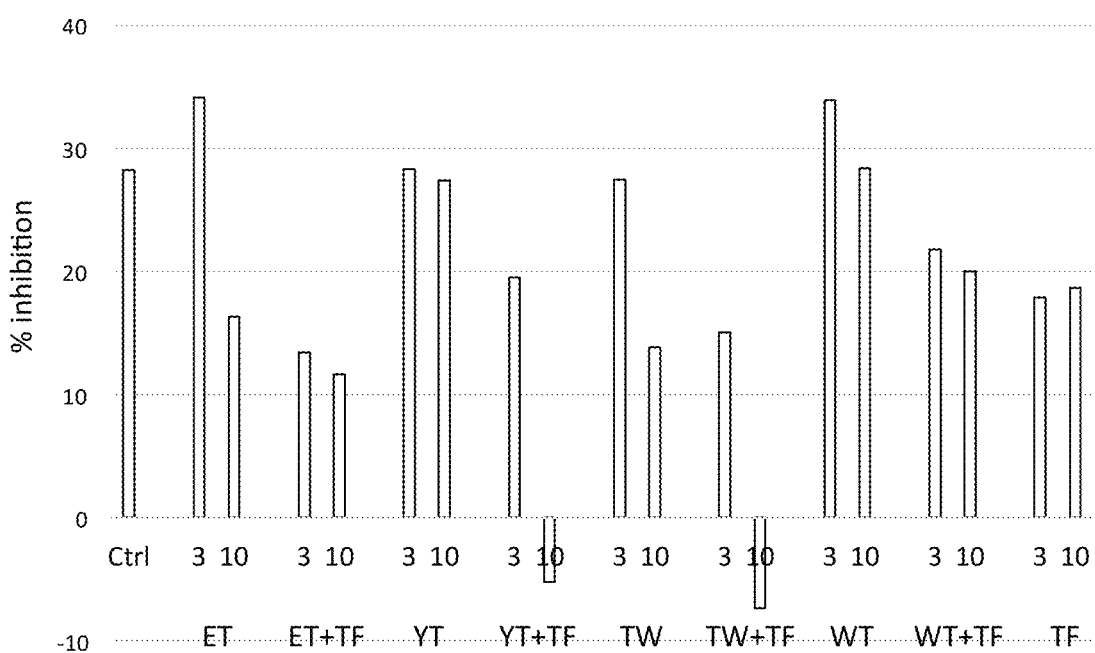
FIG. 5B summarizes the results of a cell-based assay, which shows different combinations of PD-L1 blocking peptide treatment inhibiting PD-1/PD-L1 interactions.

FIG. 5B shows cell-based assay results of different PD-L1 blocking peptide treatment inhibiting PD-1/PD-L1 interaction. In this Example, $5 \times 10^4$ Jurkat T cells were activated with 1 µ/ml of PHA and 50 ng/ml of PMA and co-cultured with $1 \times 10^5$ PD-L1-expressed tumour cells mixed with the different combinations of PD-L1 blocking peptides at 37° C. for 48 hours. Cell culture supernatants were then harvested and IL-2 production (from the Jurkat T cells) was assessed by IL-2 ELISA. As shown in FIGS. 5A and 5B, the test PD-L1 blocking peptides (and the tested combinations thereof) did exhibit inhibition of PD-1/PD-L1 interaction.

Figure 6:
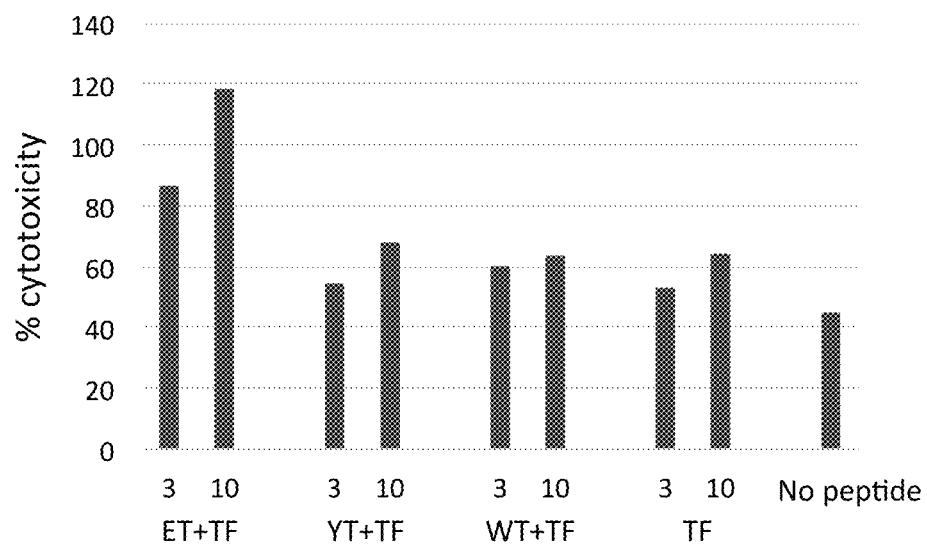
FIG. 6 summarizes the results of a cytotoxicity assay, which shows blocking PD-L1 via combined peptides enhances cytotoxicity against tumour cells.

FIG. 6 shows blocking PD-L1 through the combined peptides referenced therein enhances cytotoxicity against tumour cells. In this Example, peripheral blood mononuclear cells (PBMCs) were stimulated with anti-CD3 antibody (OKT-3) plus IL-2 for 24 hours and were subsequently incubated with PD-L1 blockers/peptides (the blockers/peptides referenced in FIG. 6) and Calcein-AM labelled H460 cells (large cell lung carcinoma) for 24 hours. Supernatants were harvested after incubation and then released calcein-AM fluorescence was measured via a microplate reader (emission 485, excitation 525). The percentage of cytotoxicity (shown in FIG. 6) was calculated based on the following formula: [(sample reading−minimum release)/(maximum release−minimum release)]×100. As shown in FIG. 6, the test PD-L1 blocking peptides exhibited enhanced cytotoxicity against the subject tumour cells (relative to the control, "no peptide"), and such activity was particularly prominent when such peptides were administered at 10 µg/ml (versus 3 µg/ml).

Figure 7:
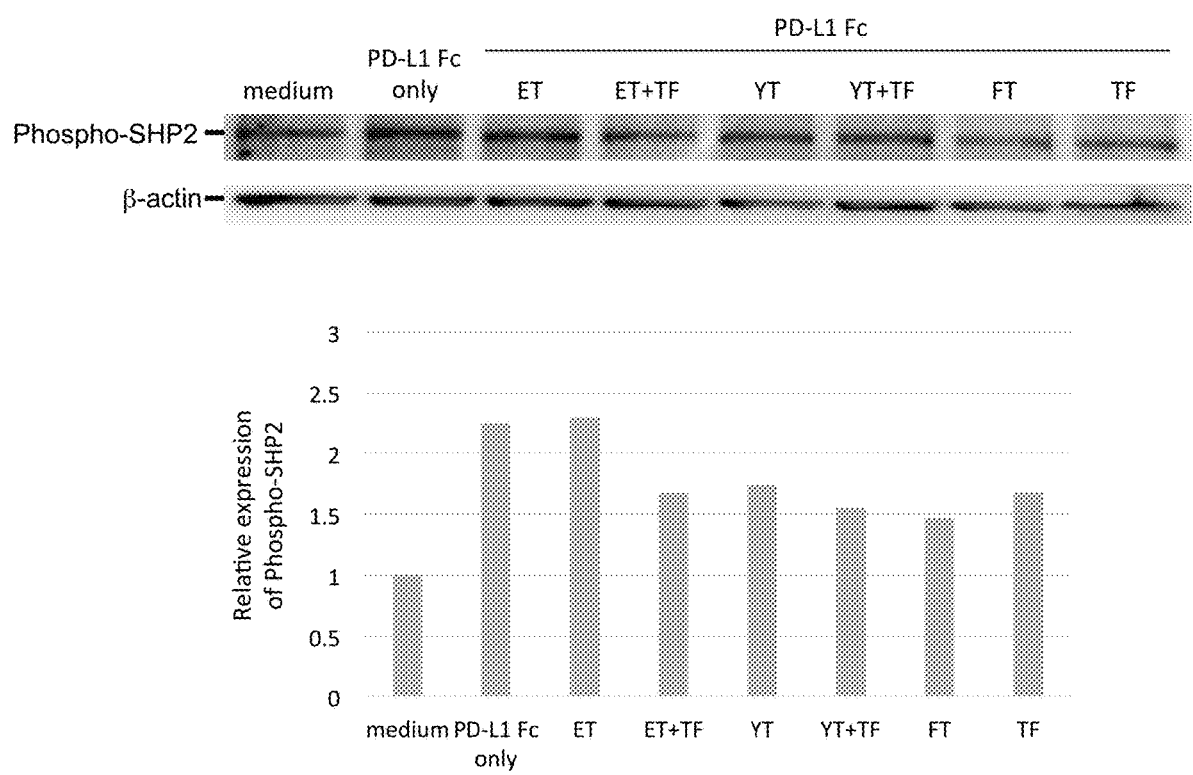
FIG. 7 summarizes the results of an assay that shows the effects of different PD-L1 blockers on levels of phosphorylated SHP-2.
Figure 8:
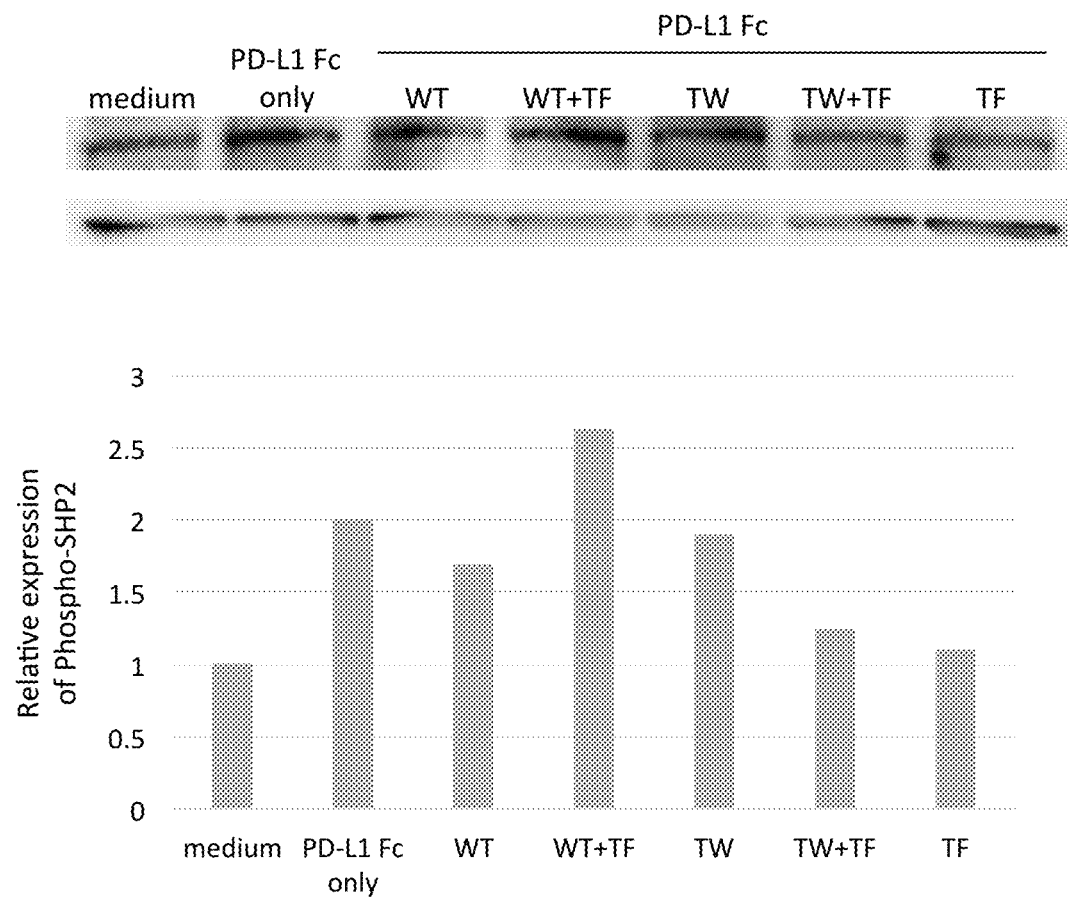
FIG. 8 summarizes the results of an assay that shows the effects of additional PD-L1 blockers on levels of phosphorylated SHP-2.

Referring now to FIGS. 7 and 8, in this Example, Jurkat cells were starved in serum-free medium overnight. The cells were subsequently cultured with different combinations of the PD-L1 blockers/peptides (referenced in FIGS. 7 and 8) or medium alone in a 96-well plate pre-coated with an anti-CD3 monoclonal antibody and PD-L1 Fc at 37° C. for 10 minutes. Cold PBS was added into each well to stop the reaction and cell lysates were prepared for blotting with anti-phosphorylated SHP-2 and anti-Beta-actin antibodies. The expression level of phosphorylated SHP-2 (a cytoplasmic SH2 domain containing protein tyrosine phosphatase) was standardized based on Beta-actin expression, and the relative expression level of phosphorylated SHP-2 for the different PD-L1 blockers was normalized using medium alone sample. As shown in FIGS. 7 and 8, a majority of the tested PD-L1 blockers/peptides were effective to increase the relative expression level of phosphorylated SHP-2.

Figures 9A, 9B:
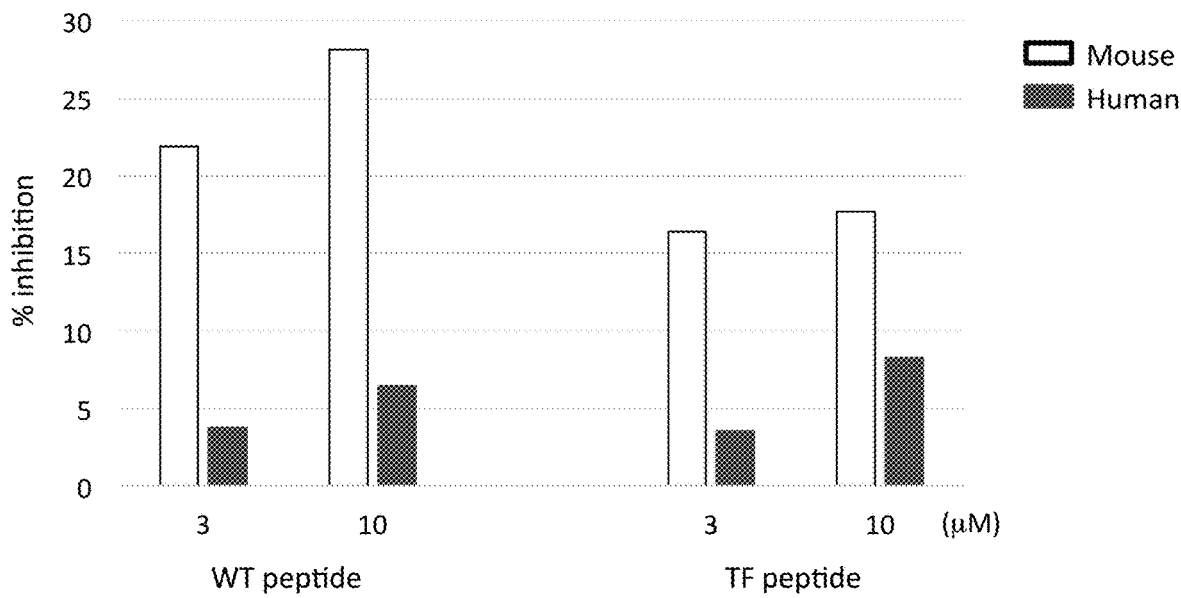
FIG. 9A summarizes the results of an assay that shows blocking mouse PD-L1 binding to mouse PD-1 by mouse peptides.
FIG. 9B shows the difference in amino acid composition between the human and mouse WT and TF peptides referenced in the Examples.

FIG. 9A shows the effects of blocking mouse PD-L1 binding to mouse PD1. More specifically, mouse and human WT and TF peptides (3 and 10 µM) were mixed with recombinant mouse PD-1 Fc and bound to a mouse PD-L1 Fc coated 96-well Immuno Maxisorp flat bottom plate. Binding was detected via a biotinylated anti-mouse PD-1 antibody, streptavidin-horseradish peroxidase (HRP), and 3,3', 5,5' Tetramethylbenzidine (TMB) substrate. Absorbance measurements were collected at 450 nm via a plate reader. The increased percent (%) of mouse (and human) PD-1/PD L1 inhibition was compared to a control (no peptide) sample. The results show specificity of the peptides—specifically, that human peptides do not have the same blocking effects as mouse peptides for mouse PD-L1. The differences between the human and mouse peptides are illustrated in FIG. 9B.

Figure 10A:
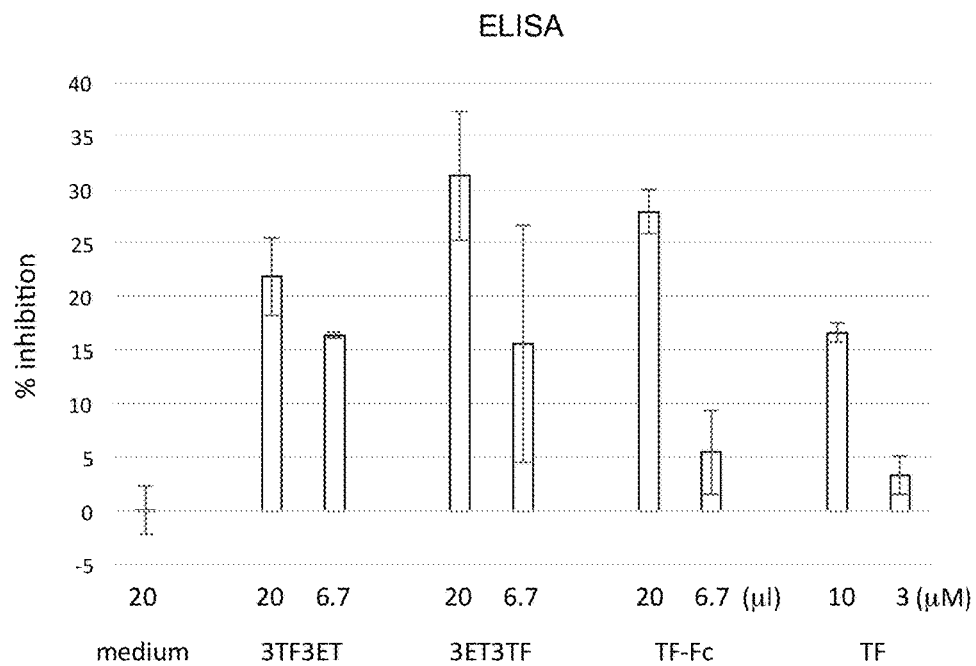
FIG. 10A summarizes the results of an ELISA assay that shows blocking PD-L1 binding to PD-1 by different forms of PD-L1 blocking peptides.

FIG. 10A shows blocking PD-L1 binding to PD-1 by different forms of PD-L1 blocking peptides. More particularly, in this Example and referring to FIGS. 10A and 10B, 3TF3ET represents three copies of TF (SEQ ID NO:2) linked to a linker followed by three copies of ET (SEQ ID NO:25); 3ET3TF represents three copies of ET peptide linked to a linker followed by three copies of TF peptide; and TF-Fc represents TF linked to a fragment crystallisable (Fc) region of human IgG4. 293FT cells were infected with PD-L1 blocking peptide-encoded viral vector for 48 hours. Each peptide (or peptide combination) was expressed and secreted from the infected cells (the peptide or peptide combination was secreted via a fused 5' signal peptide). Harvested PD-L1 blocking peptide-contained supernatants from infected 293FT cells or synthetic TF peptide were mixed with recombinant human PD-1 Fc and bound to a human PD-L1 Fc coated 96-well Immuno Maxisorp flat bottom plate. Binding was detected via a biotinylated anti-PD-1 antibody, streptavidin, horseradish peroxidase (HRP), and 3,3', 5,5'-Tetramethylbenzidine (TMB) substrate. Absorbance measurements were collected at 450 nm via a plate reader. The increased percent (%) of human PD-1/PD-L1 inhibition was compared to a control (no peptide) sample.

Figure 10B:
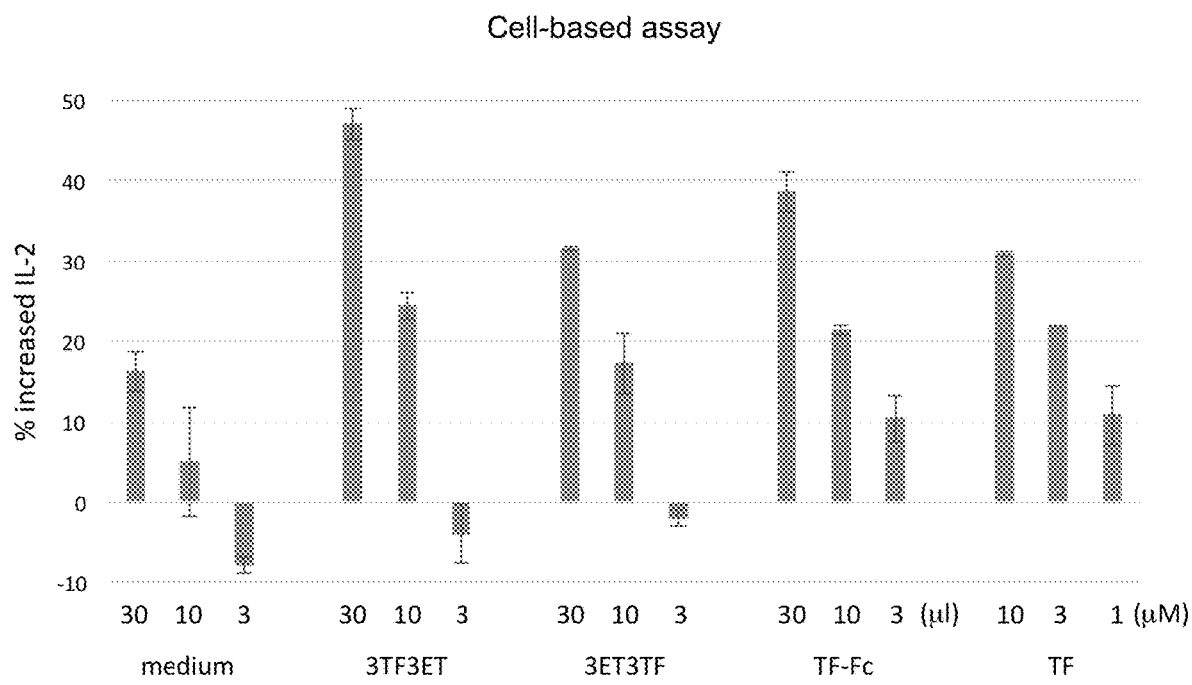
FIG. 10B summarizes the results of a cell-based assay that shows different forms of PD-L1 blocking peptide treatment inhibiting PD-1/PD-L1 interaction.

FIG. 10B shows cell-based assay results of different forms of PD-L1 blocking peptide treatment inhibiting PD-1/PD-L1 interaction. $5 \times 10^4$ Jurkat T cells were activated with 1 µ/ml of PHA and 50 ng/ml of PMA and co-cultured with $1 \times 10^5$ PD-L1-expressing tumour cells mixed with PD-L1 blocking peptide-contained supernatants or synthetic TF peptide at 37° C. for 48 hours. After 48 hours, cell culture supernatants were harvested and IL-2 production from the Jurkat T cells was assessed by IL-2 ELISA.

Figure 11:
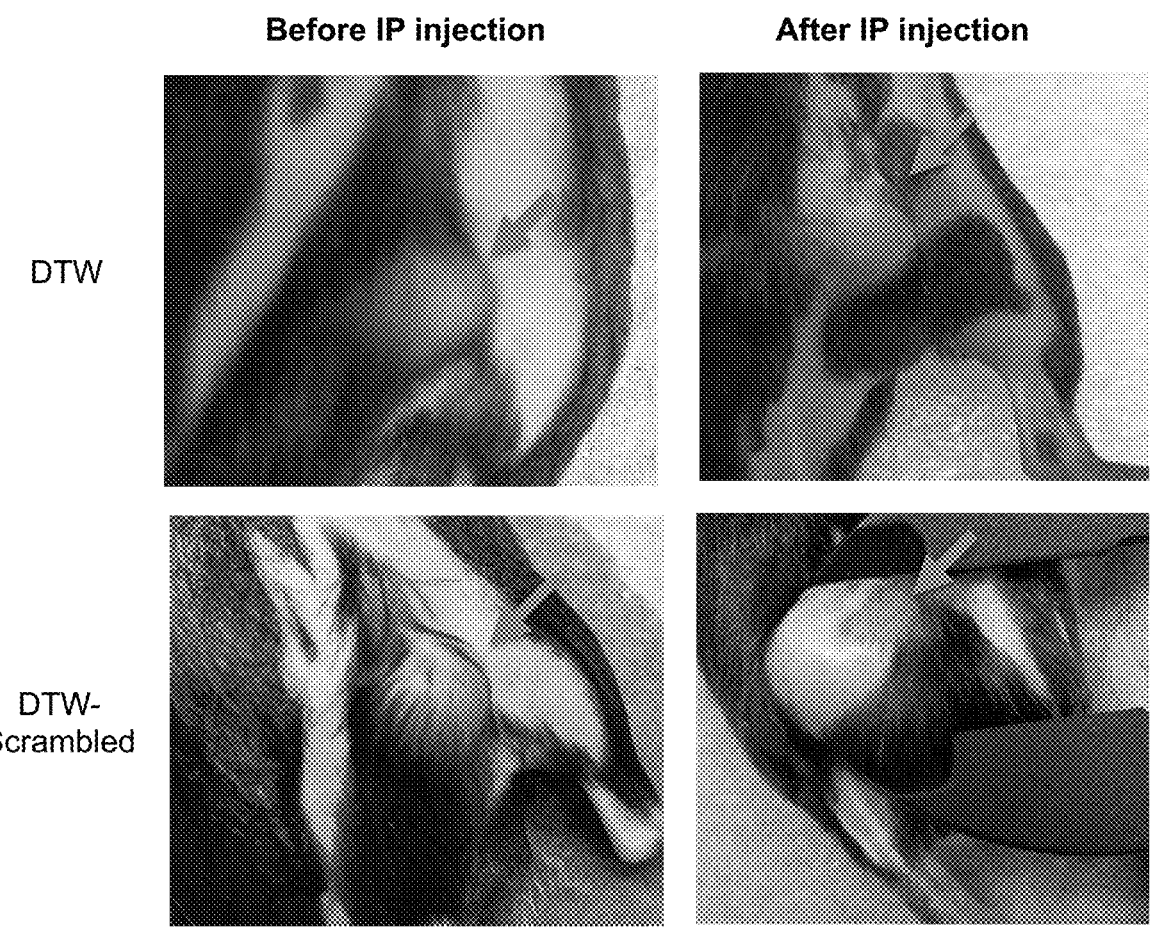
FIG. 11 shows the results of an in vivo experiment, showing the effects of D-TW on mice harbouring tumour cell line LL/2.
Figure 12:
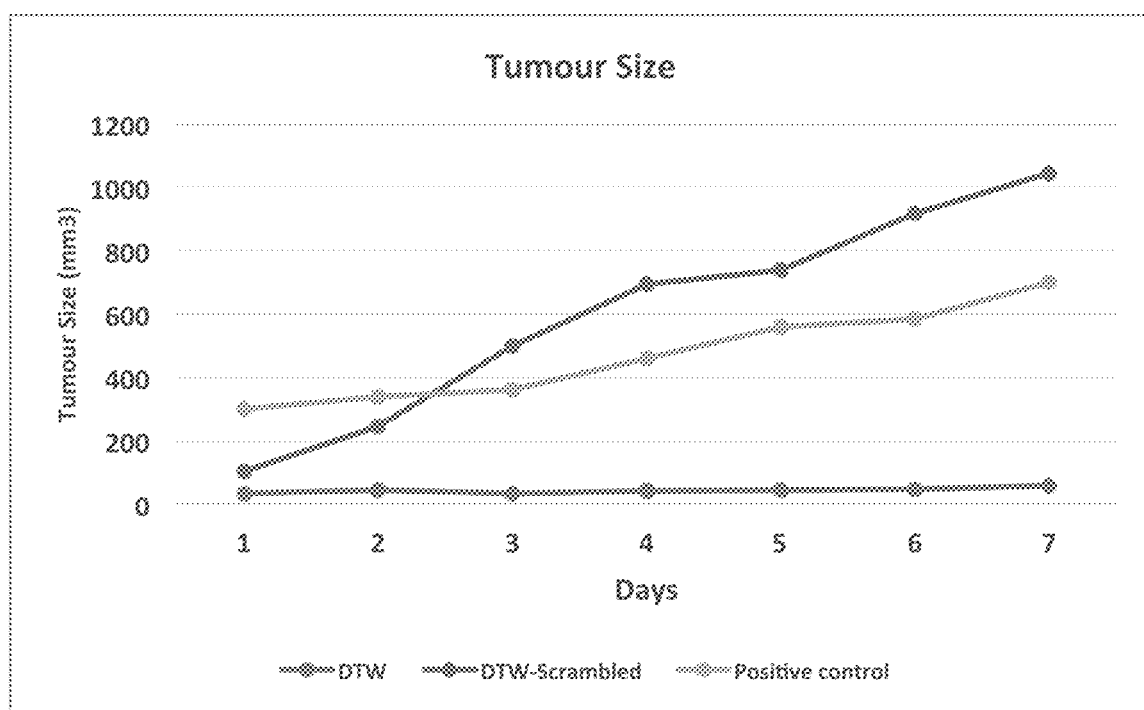
FIG. 12 shows the results of an in vivo experiment, showing the effects of D-TW on tumour size in the mouse model referenced in FIG. 11.

FIG. 11 shows the results of an in vivo experiment, showing the effects of D-TW on mice harbouring tumour cell line LL/2. More particularly, mice strain C57Bl/6 (male, 4-weeks, initial body weight ~20-22 g) were inoculated with tumour cell line LL/2, at S.C. $10^5$ per mouse. After 14 days post-implantation, the mice were treated with D-TW or D-TW-Scrambled for 7 days (at 200 mg/kg), via intraperitoneal (IP) injection. FIG. 12 shows the effects of D-TW on tumour size in the mice referenced in FIG. 11. As shown in FIG. 12, it was found that the D-TW peptide is generally non-toxic to the C57Bl/6 mouse strain. In addition, the results show that the D-TW peptide (at 200 mg/kg) inoculation was effective to significantly inhibit tumour growth (relative to the control and relative to the D-TW-Scrambled peptide).

The many aspects and benefits of the invention are apparent from the detailed description, and thus, it is intended for the following claims to cover all such aspects and benefits of the invention, which fall within the scope and spirit of the invention. In addition, because numerous modifications and variations will be obvious and readily occur to those skilled in the art, the claims should not be construed to limit the invention to the exact construction and operation illustrated and described herein. Accordingly, all suitable modifications and equivalents should be understood to fall within the scope of the invention as claimed herein.

What is claimed is:

1. A method for inhibiting an interaction between programmed death-1 protein (PD-1) and programmed death-ligand 1 (PD-L1) in a cell by administering one or more peptides to the cell, wherein each of said peptides consists of one of the amino acid sequences selected from the group consisting of SEQ ID NO:1-SEQ ID NO:36.

2. The method of claim 1, wherein each of said peptides consists of one or more amino acid sequences that are selected from the group consisting of SEQ ID NO:1, SEQ ID NO:2, SEQ ID NO:25, SEQ ID NO:28, and SEQ ID NO:34.

3. The method of claim 2, wherein the peptide is disposed within a pharmaceutical-grade composition.

4. The method of claim 3, wherein the peptide is formulated to be administered to a mammal via local tissue injection, intravenous injection or intraperitoneal injection.

5. The method of claim 2, wherein the peptide is encoded by a viral or non-viral vector and secreted into an extracellular space.

6. A method for treating breast cancer, lung cancer, melanoma, or renal cancer in a subject by administering one or more peptides to the subject, wherein each of said peptides consists of one or more of the amino acid sequences that are selected from the group consisting of SEQ ID NO:1-SEQ ID NO:36.

7. The method of claim 6, wherein each of said peptides consists of one or more amino acid sequences that are selected from the group consisting of SEQ ID NO:1, SEQ ID NO:2, SEQ ID NO:25, SEQ ID NO:28, and SEQ ID NO:34.

8. The method of claim 7, wherein the peptide is disposed within a pharmaceutical-grade composition.

9. The method of claim 8, wherein the peptide is formulated to be administered to a mammal via local tissue injection, intravenous injection or intraperitoneal injection.

10. The method of claim 7, wherein the peptide is encoded by a viral or non-viral vector and secreted into an extracellular space.

* * * * *

SEQUENCE LISTING

<160> NUMBER OF SEQ ID NOS: 36

<210> SEQ ID NO 1
<211> LENGTH: 10
<212> TYPE: PRT
<213> ORGANISM: Artificial Sequence
<220> FEATURE:
<223> OTHER INFORMATION: Synthesized

<400> SEQUENCE: 1

Trp Tyr Arg Met Ser Pro Ser Asn Gln Thr
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthesized

<400> SEQUENCE: 2

Thr Ala His Pro Ser Pro Ser Pro Arg Ser Ala Gly Gln Phe
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthesized

<400> SEQUENCE: 3

Trp Tyr Arg Met Ser Pro Ser Asn Gln Asp
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthesized

<400> SEQUENCE: 4

Trp Tyr Arg Met Ser Pro Ser Asn Gln Glu
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthesized

<400> SEQUENCE: 5

Trp Tyr Arg Met Ser Pro Ser Asn Asp Thr
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthesized

<400> SEQUENCE: 6

Trp Tyr Arg Met Ser Pro Ser Asn Glu Thr
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthesized

<400> SEQUENCE: 7

Trp Tyr Arg Met Ser Pro Ser Glu Gln Thr
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthesized

<400> SEQUENCE: 8

Trp Tyr Arg Met Ser Pro Asp Asn Gln Thr
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthesized

<400> SEQUENCE: 9

Trp Tyr Arg Met Ser Pro Glu Asn Gln Thr
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthesized

<400> SEQUENCE: 10

Trp Tyr Arg Met Ser Pro Pro Asn Gln Thr
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthesized

<400> SEQUENCE: 11

Trp Tyr Arg Met Ser Asp Ser Asn Gln Thr
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthesized

<400> SEQUENCE: 12

Trp Tyr Arg Met Ser Glu Ser Asn Gln Thr
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthesized

<400> SEQUENCE: 13

Trp Tyr Arg Met Ala Pro Ser Asn Gln Thr
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthesized

<400> SEQUENCE: 14

Trp Tyr Arg Met Gln Pro Ser Asn Gln Thr
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthesized

<400> SEQUENCE: 15

Trp Tyr Arg Met Met Pro Ser Asn Gln Thr
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthesized

<400> SEQUENCE: 16

Trp Tyr Arg Met Pro Pro Ser Asn Gln Thr
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthesized

<400> SEQUENCE: 17

Trp Tyr Arg Asp Ser Pro Ser Asn Gln Thr
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthesized

<400> SEQUENCE: 18

Trp Tyr Arg Glu Ser Pro Ser Asn Gln Thr
1               5                   10

```
<210> SEQ ID NO 19
<211> LENGTH: 10
<212> TYPE: PRT
<213> ORGANISM: Artificial Sequence
<220> FEATURE:
<223> OTHER INFORMATION: Synthesized

<400> SEQUENCE: 19

Trp Tyr Ile Met Ser Pro Ser Asn Gln Thr
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthesized

<400> SEQUENCE: 20

Trp Tyr Leu Met Ser Pro Ser Asn Gln Thr
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthesized

<400> SEQUENCE: 21

Trp Tyr Tyr Met Ser Pro Ser Asn Gln Thr
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthesized

<400> SEQUENCE: 22

Trp Tyr Val Met Ser Pro Ser Asn Gln Thr
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthesized

<400> SEQUENCE: 23

Asp Tyr Arg Met Ser Pro Ser Asn Gln Thr
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthesized

<400> SEQUENCE: 24

Gln Tyr Arg Met Ser Pro Ser Asn Gln Thr
1               5                   10

<210> SEQ ID NO 25
```

```
<211> LENGTH: 10
<212> TYPE: PRT
<213> ORGANISM: Artificial Sequence
<220> FEATURE:
<223> OTHER INFORMATION: Synthesized

<400> SEQUENCE: 25

Glu Tyr Arg Met Ser Pro Ser Asn Gln Thr
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthesized

<400> SEQUENCE: 26

Met Tyr Arg Met Ser Pro Ser Asn Gln Thr
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthesized

<400> SEQUENCE: 27

Thr Tyr Arg Met Ser Pro Ser Asn Gln Thr
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthesized

<400> SEQUENCE: 28

Tyr Tyr Arg Met Ser Pro Ser Asn Gln Thr
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthesized

<400> SEQUENCE: 29

Trp Tyr Arg Met Ser Trp Ser Asn Gln Thr
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthesized

<400> SEQUENCE: 30

Trp Tyr Arg Met Tyr Pro Ser Asn Gln Thr
1               5                   10

<210> SEQ ID NO 31
<211> LENGTH: 10
```

```
<212> TYPE: PRT
<213> ORGANISM: Artificial Sequence
<220> FEATURE:
<223> OTHER INFORMATION: Synthesized

<400> SEQUENCE: 31

Trp Tyr Arg Asn Ser Pro Ser Asn Gln Thr
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Synthesized

<400> SEQUENCE: 32

Trp Tyr Thr Met Ser Pro Ser Asn Gln Thr
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Synthesized

<400> SEQUENCE: 33

Phe Gln Gly Ala Ser Arg Pro Ser Pro His Ala Thr
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Synthesized

<400> SEQUENCE: 34

Thr Gln Asn Ser Pro Ser Met Arg Tyr Trp
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthesized

<400> SEQUENCE: 35

Trp Asn Arg Leu Ser Pro Ser Asn Gln Thr
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Synthesized

<400> SEQUENCE: 36

Thr Arg Tyr Pro Ser Pro Ser Pro Lys Pro Glu Gly Arg Phe
1               5                   10
```